US010835494B2

(12) United States Patent
López Machado et al.

(10) Patent No.: US 10,835,494 B2
(45) Date of Patent: Nov. 17, 2020

(54) LIPOSOMES FOR THE TREATMENT OF OCULAR DISEASES

(71) Applicant: TDC Technology Dedicated to Care srl, Milano MI (IT)

(72) Inventors: Ana Laura López Machado, Santa Cruz de Tenerife (ES); Elena Sánchez López, Barcelona (ES); Maria Luisa Garcia Lopez, Barcelona (ES); Martina Biancardi, Barcelona (ES)

(73) Assignee: TDC Technology Dedicated to Care srl, Milan (IT)

( * ) Notice: Subject to any disclaimer, the term of this patent is extended or adjusted under 35 U.S.C. 154(b) by 0 days.

(21) Appl. No.: 16/527,245

(22) Filed: Jul. 31, 2019

(65) Prior Publication Data
US 2020/0046641 A1 Feb. 13, 2020

(30) Foreign Application Priority Data
Jul. 31, 2018 (IT) .................... 102018000007677

(51) Int. Cl.
*A61K 9/127* (2006.01)
*A61P 27/02* (2006.01)
*A61K 9/00* (2006.01)
*A61K 47/36* (2006.01)

(52) U.S. Cl.
CPC .......... *A61K 9/1276* (2013.01); *A61K 9/0048* (2013.01); *A61K 47/36* (2013.01); *A61P 27/02* (2018.01)

(58) Field of Classification Search
CPC .... A61K 9/19; A61K 2300/00; A61K 31/496; A61K 9/1271; A61K 31/4196; A61P 1/16; A61P 29/00; A61P 31/00; A61P 31/04; A61P 31/14; A61P 31/08; A61P 17/04
See application file for complete search history.

(56) References Cited

U.S. PATENT DOCUMENTS

2012/0003296 A1* 1/2012 Shantha ............... A61K 39/395
424/450

FOREIGN PATENT DOCUMENTS

EP 2 016 937 1/2009

OTHER PUBLICATIONS

Marta Vi Cario-D E- La-Torre et al: 11 Novel Nano- Li posome Formulation for Dry Eyes with Components Similar to the Preocular Tear Film 11, Polymers, vol. 10, No. 4, Apr. 11, 2018, p. 425.
Fujihara T et al : 11 Lactoferrin suppresses loss of corneal epithelial integrity in a rabbit short-term dry eye model 11, Journal of Ocular Pharmacology Ano Therapeut, Mary Ann Liebert, Inc., New York, NY, US, vol. 14, No. 2, Jan. 1, 1998 (Jan. 1, 1998), pp. 99-107.
Lin et al: "Liposome coated with low molecular weight chitosan and its potential use in ocular drug delivery", International Journal of Pharmaceutics, Elsevier, NL, vol . 379, No. I , Sep. 8, 2009 (Sep. 8, 2009), pp. 131-138.
Trif M et al: "Liposomes as possible carriers for lactoferrin in the local treatment of inflammatory diseases", Proceedings of the Society for Experimental Biology Ano Medicine, Sage Publications Ltd, GB, vol. 226, No. 6, Jan. 1, 2001.
European search report issued by the EPO for corresponding EP application No. 19189078 dated Dec. 3, 2018.
Search Report issued by the EPO for Italian priority application No. IT2108 00007677 dated Mar. 29, 2019.

* cited by examiner

Primary Examiner — Nannette Holloman
(74) Attorney, Agent, or Firm — Silvia Salvadori

(57) ABSTRACT

The invention refers to a product made of liposomes which comprises lactoferrin and a component selected from hyaluronic acid or chitosan, as active ingredients, as well as to compositions comprising it and their use in the prevention and/or treatment of diseases related to the eye, such as for example the ocular diseases characterized by the presence of an inflammatory condition.

10 Claims, 2 Drawing Sheets

LIPOSOMES FOR THE TREATMENT OF OCULAR DISEASES

STATE OF THE ART

Ocular diseases are diseases concerning one or more eye structures. Among them, there are more or less severe diseases, such as for example the inflammatory diseases, hyposphagma and the dry eye syndrome (or more simply, dry eye).

The ocular inflammatory diseases are pathologies characterized by the inflammation of one or more eye structures. They can occur at the level of internal and/or external structures at the eyeball. In particular, the ocular inflammatory diseases are characterized by the presence of an inflammatory process arising in different areas of the eye. Some of the main ocular inflammatory diseases are, for example, conjunctivitis, chalazion, stye, blepharoconjunctivitis and keratitis.

Hyposphagma, or subconjunctival hemorrhage, is characterized by bleeding under the conjunctiva.

The dry eye syndrome is a disease characterized by the quantitative and/or qualitative reduction of tear film.

The therapy for the treatment of the ocular diseases varies according to the type of pathology, e.g. depending on the type and severity of the inflammation. The most used drugs for the treatment of such kind of pathologies and their complications are mainly antibiotics for topical use, ocular lubricants, steroidal anti-inflammatory drugs and, in the most severe cases, orally taken drugs.

However, the use of the above mentioned drugs has some disadvantages. For example, the prolonged use of some antibiotics for topical use can limit or cure the ocular microbiological infection, but at the same time can involve an acute inflammation of the external tunic (fibrous tunic) of the eye, with redness and itch symptoms. Moreover, a prolonged use of the antibiotic can favor the occurrence of bacterial strains resistant to the active ingredient used (antimicrobial resistance event). Moreover, the drugs containing steroidal anti-inflammatory drugs have notoriously typical side-effects, which involve, for example, the glucidic, protein, lipid and bone metabolisms, the kidney excretion of sodium and potassium, the gastric acid excretion, the blood crasis and the mood. Finally, the orally taken drugs usually require a higher dose with respect to the topically taken drugs, in order to provide the same concentrations in the area of interest. Moreover, the orally taken drugs are more prone to provide side-effects at the systemic level, since they are absorbed at the gastrointestinal level and are delivered in all the organism districts through the systemic circulation.

In view of the disadvantages of the above stated conventional drugs, novel ocular compositions which allow to overcome such disadvantages and that show efficacy capable of preventing, alleviating and/or solving such diseases are nowadays required.

OBJECTS OF THE INVENTION

Object of the present invention is to provide a product which can prevent, alleviate and/or treat the ocular diseases, in particular hyposphagma, dry eye syndrome, inflammatory ocular diseases and their related complications.

Further object of the present invention is to provide a pharmaceutical composition, preferably for topical use, more preferably for ocular topical use, which comprises the above product and which is used for the prevention and/or treatment of the ocular diseases.

DESCRIPTION OF THE INVENTION

The objects stated above, as well as other objects, are achieved by means of the object of the present invention, i.e. a product constituted by liposomes that comprises lactoferrin and a component selected from hyaluronic acid or chitosan, as active ingredients. As it will be shown in the experimental section, the product of the invention is useful for the treatment of ocular diseases.

In the present invention, with the term "liposome" it is meant a vesicle consisting of at least one lipid bilayer and one core of aqueous solution encapsulated within the lipid bilayer. The lipids constituting the liposome bilayer (or liposome-forming lipids) can comprise mixtures composed essentially of phospholipids, such as for example phosphatidylcholine, and cholesterol in a lower amount. By way of example, lipids useful to constitute the lipid bilayer of liposome are a mixture of cholesterol and sodium lecithin comprising 70% phosphatidylcholine (such as for example the commercial product Lipoid S75, or the commercial product Lipoid S80, currently commercialized by the Lipoid Kosmetik AG Company, DE). The liposome can also comprise, in its lipid bilayer, further compounds of non-lipid nature, e.g. other organic compounds (such as tocopherol).

Lactoferrin comprised in the liposomes according to the invention is preferably encapsulated inside the lipid bilayer, and more preferably it is solubilized in the core of aqueous solution which is typically inside the lipid bilayer.

The product of the invention, constituted by liposomes, can comprise, in addition to lactoferrin, a component selected from hyaluronic acid or chitosan.

According to a particular aspect of the invention, when the product comprises hyaluronic acid as component, chitosan can also be comprised, and vice versa. In other words, the products of the invention can comprise lactoferrin and hyaluronic acid in combination with chitosan; or alternatively the products of the invention can comprise lactoferrin and chitosan in combination with hyaluronic acid.

When the product of the invention comprises hyaluronic acid, the hyaluronic acid can also be outside the lipid bilayer of liposomes.

According to another embodiment, when the product of the invention comprises hyaluronic acid, the hyaluronic acid is encapsulated inside the lipid bilayer and solubilized in the core of aqueous solution inside the liposome lipid bilayer.

When the products of the invention comprise chitosan, such chitosan preferably forms a coating of the lipid bilayer of the liposomes.

As already mentioned, the product of the invention, as well as the compositions comprising it, has prophylactic and therapeutic properties towards diseases, and in particular towards ocular diseases.

It has been surprisingly found that the products of the invention show therapeutic and prophylactic effects against inflammation, and in particular ocular inflammation. Such effects are demonstrated in the experimental section. Still as demonstrated in the experimental section, it was surprisingly observed that the therapeutic and prophylactic effects against the ocular inflammation characterizing the products according to the invention, are not obtained instead by comparative solutions comprising free lactoferrin, i.e. lactoferrin not encapsulated into the lipid bilayer of the liposomes.

It was also surprisingly found that the products of the invention are particularly effective in alleviating and/or curing the symptoms of hyposphagma and dry eye syndrome.

The product of the invention has in addition various advantages which makes it particularly stable and effective for its use in the eye. For example, lactoferrin, which is a glycoprotein belonging to the ferritin family, is stabilized thanks to its incorporation into the liposomes, according to the invention, and is therefore protected against a possible denaturation.

Hyaluronic acid, which is comprised in the product of the invention, effectively lubricates the ocular surface and favors the regeneration of the corneal epithelium.

Also, the liposomes assist and favor the ocular adhesion process, thus favoring the topic permanence and the delivery of lactoferrin and of the other components comprised in it.

It was also found that chitosan, which preferably coats the lipid bilayer of the liposomes, favors a sustained release of the components encapsulated into the lipid bilayer of the liposomes, such as for example of lactoferrin.

It was also observed, by means of ocular tolerance tests, that the product of the invention is biocompatibile when topically applied at ocular level, as it is demonstrated in the experimental section. As a matter of fact it does not cause undesired inflammatory effects. For this reason, the product of the invention, consisting of liposomes as described above, can be formulated in compositions which can be topically administered, which allow lactoferrin and the other components comprised in it to be vehiculated, such as for example hyaluronic acid, directly to the area of interest, i.e. the eye. This provides to the product of the invention all the typical advantages of the topical formulations.

Preferably, the lipids constituting the bilayer confer to the liposomes a positive surface electrical charge. Such electrical charge is advantageous for the ocular topical administration, since it is responsible of the adhesion of the liposome to the eye by electrostatic attraction. Therefore, the liposome-forming lipids advantageously have such a positive charge to confer positive surface electrical charge to the liposomes according to the invention. An indicator of such positive charge is the Z-potential. Advantageously, the Z-potential charge of the liposomes according to the invention, when suspended in an aqueous medium, can be greater than 0 mV, preferably can be greater than or equal to 10 mV, more preferably can be greater than or equal to 15 mV, still more preferably can be greater than or equal to 20 mV. For example, the Z-potential charge of the liposomes can be in the range from 25 to 30 mV. The Z-potential values as described above can be advantageously measured by using a particle analyzer by means of the laser Doppler electrophoresis technique, e.g. by means of the Zetasizer Nano ZS instrument by Malvern Panalytical.

The liposomes according to the invention have preferably a size lower than or equal to 200 nm, more preferably lower than or equal to 150 nm, still more preferably lower than or equal to 100 nm, still more preferably in the range from 70 nm to 100 nm. The sizes as described above can be advantageously measured by using a particle analyzer by means of the dynamics light scattering technique (DLS), e.g. by means of the Zetasizer Nano ZS instrument by Malvern Panalytical. Such measurements can be carried out after appropriately diluting the liposomes, e.g. with a 1:10 dilution with distilled water. The sizes described above allow a composition comprising the product according to the invention, being it as well object of the present invention, not to cause irritation or other unfavorable effects to the ocular microenvironment when it is administered by ophthalmic topical route.

According to the present invention, preferred hyaluronic acids are those with a low/intermediate/high molecular weight, e.g. those with a molecular weight in the range from 20 kDa to 1500 kDa, or those with a molecular weight in the range from 800 kDa to 2000 kDa, preferably from 100 kDa to 1000 kDa, or preferably in the range from 1500 kDa to 2000 kDa, more preferably it is about 290 kDa, or more preferably it is about 1600 kDa. The hyaluronic acids having the molecular weight above are commercially available. The molecular weight of such hyaluronic acids can be determined by means of conventional methods, e.g. by means of gel permeation chromatography. Gel permeation chromatography (GPC) is a type of size exclusion chromatography (SEC). It was found that the use of hyaluronic acid with molecular weight as described above allows higher encapsulation efficiency of the protein (lactoferrin) inside the liposome to be obtained.

The hyaluronic acid can be also comprised in the product of the invention in the form of a pharmaceutically acceptable salt thereof.

The product according to the invention can comprise, in its base formulation, agents suitable to modulate its viscosity and/or preservatives and/or stabilizing agents and/or agents suitable to modulate its osmolarity.

The liposomes can also incorporate pharmaceutically suitable functional agents, such as for example cryoprotectants, osmolarity modulators, surfactants and buffers.

The cryoprotectants allow to maintain unaltered the chemical-physical characteristics of the liposomes, as well as of the compositions comprising them. Indeed, cryoprotectants are useful, e.g., if the liposomes have to be freeze-dried to be long-term stored. Cryoprotectants useful in the present invention can be, for example, mannitol, trehalose and cyclodextrin, and preferably are trehalose and cyclodextrin. According to the present invention, a particularly advantageous cyclodextrin is hydroxypropyl-β-cyclodextrin.

Osmolarity modulators allow to the core of aqueous solution, once it has been released, to avoid osmotic stresses to the ocular microenvironment. Advantageously, the osmolarity modulators confer to the core of aqueous solution such an osmolarity to be hypotonic or isotonic relative to the ocular microenvironment. Osmolarity modulators useful in the present invention can be cationic electrolytes, among which Na, K, Ca, Mg, and sugars and/or polyalcohols, such as for example mannitol, trehalose and cyclodextrin, trehalose and cyclodextrin being preferred.

Advantageously, the cryoprotectants can also be osmolarity modulating agents, such as for example mannitol, trehalose and cyclodextrin.

Cyclodextrin is a particularly useful functional agent according to the present invention, both incorporated inside the liposomes and comprised in a composition comprising the product of the invention. Cyclodextrin assists the protein solubilization and stabilization, such as for example of lactoferrin, and contributes to the osmolarity of the core of aqueous solution of the liposomes and/or composition of the invention. Moreover, cyclodextrin allows to favor the freeze-drying process, as it is a cryoprotectant, and protects and increases the stability of lactoferrin incorporated in the liposome.

Advantageously, the core of aqueous solution inside liposomes can have an osmolarity comprised in a range from 200 to 500 mOsm/Kg, preferably from 250 to 450 mOsm/

Kg, and more preferably it is about 310 mOsm/Kg. Alternatively, the osmolarity can be about 275 mOsm/Kg for the liposomes comprising hyaluronic acid, and about 420 mOsm/Kg for the liposomes comprising chitosan. Such osmolarity values can be measured by means of conventional instruments, such as for example Advanced® Model 3320 Micro-Osmometer (Advanced® Instruments, Inc., Norwood, Mass., USA). The liposomes comprising a core of aqueous solution that have the above osmolarity, avoid to cause osmotic stresses to the ocular microenvironment once they are administered by ocular topical route. Such osmolarity can be adjusted by osmolarity modulators as described above, e.g. to make the liposomes and/or the composition of the invention suitable for the ophthalmic administration and compliant with Phrmacopoeia requirements.

Further functional agents useful in the present invention, in particular for the preparation of the liposomes, are the surfactants. Advantageously, surfactants according to the present invention can be ionic or nonionic surfactants, preferably nonionic, such as for example the polysorbate 80 (also named Tween® 80).

The liposomes according to the invention can be prepared by means of conventional techniques, e.g. those described in the experimental section.

In particular, as described in the experimental section, the liposomes can be prepared by means of the lipid film hydration method. Such method includes the preparation of an organic phase containing the liposome-forming lipids, and at the same time the preparation of an aqueous phase comprising the components which will compose the core of aqueous solution, such as for example lactoferrin, hyaluronic acid (if present) and other functional agents (e.g., cryoprotectants). It has been observed that the order of addition of the components to the aqueous phase dose not significantly change the characteristics (size, polydispersity index and Z-potential) of the obtained liposomes, and therefore it is possible to prepare the aqueous phase by adding the components comprised in it in any order.

It has also been observed that the liposomes can be prepared without the use of an ultrasonic probe. The ultrasonic probe can cause the release of metals which could later be chelated by lactoferrin, thus making the product partially inactive. Therefore, advantageously, for the preparation of the liposomes, according to the present invention, an ultrasonic bath can be used (e.g., the ultrasonic bath Transsonic Digitals, produced by Elma GmbH).

Further object of the invention is a composition comprising the product of the invention according to the description above and pharmaceutically suitable excipients.

The composition according to the invention can comprise agents suitable to modulate its viscosity and/or preservatives and/or stabilizing agents and/or agents suitable to modulate its osmolarity.

The composition of the invention is particularly advantageous when used to prevent and/or treat ocular diseases, in particular hyposphagma, dry eye syndrome and ocular inflammatory diseases and complications thereof, and therefore said pharmaceutically suitable excipients will be excipients conventionally used in ocular topical compositions.

Compositions for ophthalmic topical use according to the invention can be suspensions of liposomes in an aqueous medium of suitable viscosity, e.g. in order to prepare eye drops.

With the term "ocular topical compositions" or "ophthalmic topical compositions" it is meant compositions directly administered to the eye, preferably at the anterior area of the external tunic (or fibrous tunic) of the eye and/or in the conjunctival sac.

The liposomes used in the composition of the invention have advantageously a positive surface charge, in order to improve their adhesion to the ocular microenvironment, in particular to the fibrous tunic of the eye; they can have a Z-potential value as described above.

The osmolarity of the composition of the invention can advantageously have the osmolarity values set forth above. The composition of the invention having the above osmolarity avoids to cause osmotic stresses to the ocular microenvironment once it is administered by ocular topical route. Such osmolarity can be regulated by means of osmolarity modulators as described above, e.g. in amounts from 1 to 30%, preferably from 5 to 25%, more preferably from 7 to 20%. By way of example, it has been found that it is possible to obtain a final osmolarity value of about 300 mOsm/kg when the composition of the invention comprising liposomes comprising hyaluronic acid contains about 9.93% hydroxypropyl-β-cyclodextrin and about 7% trehalose. Still by way of example, it has been found that it is possible to obtain a final osmolarity value of about 300 mOsm/kg when the composition of the invention comprising liposomes comprising chitosan contains about 5% hydroxypropyl-β-cyclodextrin and about 5% trehalose.

In the present invention, the percentage amounts of the components, unless otherwise specified, refer to the weight percent of the components to the total volume of the final composition (or formulation).

Advantageously, the composition of the invention can comprise:
I) liposome-forming lipids in an amount in the range from 1% to 5%, preferably from 2% to 4%, more preferably 3%; and
II) lactoferrin in an amount in the range from 0.5% to 8%, preferably from 1% to 4%, still more preferably of 2%; and a component selected from
III) hyaluronic acid in an amount in the range from 0.0001% to 0.5%, preferably from 0.0005% to 0.1%, more preferably from 0.001% to 0.02%, still more preferably of 0.01%; or
IV) chitosan in an amount in the range from 0.02% to 2%, preferably from 0.1% to 1%, more preferably of 0.2%.

Preferably, the composition of the invention can comprise liposome-forming lipids in the amount of 1.5%.

Preferably, the composition of the invention can comprise lactoferrin in the amount of 0.8%.

As it is possible to observe in the experimental section, compositions of the invention comprising the above stated amounts proved to be effective in the prevention and/or treatment of ocular diseases.

The composition of the invention can be prepared by means of conventional methods for the preparation of compositions comprising liposomes.

Advantageously, according to the present invention, the composition and/or the core of aqueous solution inside the liposomes can have a neutral or slightly acidic pH, e.g. a pH between 5 and 8, preferably between 5.4 and 7, when the composition of the invention is applied at the ocular topical level. Therefore, the composition of the invention and/or the product of the invention can have, as functional agents, also pH modulators, such as for example buffers. Such pH modulators can be present in an amount suitable to provide the desired pH based on the type of administration and/or product of the invention, e.g. the pH as described above.

The composition of the invention, as well as the products contained in it, in order to be administered by ocular topical route, may require to be sterile or essentially sterile, e.g. to fulfill the regulatory requirements. For this purpose, it is possible to sterilize the composition of the invention, as well as the liposomes contained in it, by γ-ray irradiation, e.g. at a dose of 25 kGy, or 10 kGy.

In order to increase the stability of the composition of the invention, as well as of the liposomes contained in it, it is possible to freeze-drying the composition and the liposomes. An example of freeze-drying process of the composition of the invention is provided in the experimental section.

It is further an object of the present invention the composition of the invention, as well as the product of the invention, for their use as medicament.

Indeed, as it can be observed in the experimental section, the composition of the invention and the products comprised in it are useful to prevent and/or treat the ocular diseases. For example, the product of the invention, as well as the compositions of the invention comprising the product of the invention, proved to be useful in the prevention and the treatment of the ocular inflammatory diseases.

In the present invention, with "inflammation" it is meant the known natural non-specific defense mechanism which can come after the detrimental action of physical, chemical and/or biological agents. With "ocular inflammation" or "ocular inflammatory diseases" it is meant the inflammation as described above which affects any structure of the eye (e.g., posterior chamber, ciliary area, pupil, anterior chamber, cornea, iris, crystalline lens capsule and nucleus, conjunctiva, retina vessels, optic nerve, sclera and retina). Examples of the ocular inflammatory diseases can be conjunctivitis, chalazion, stye, blepharoconjunctivitis and keratitis.

Due to the efficacy of the composition and product of the invention in the treatment of the inflammation, the composition and the product of the invention can also be used in the diseases due to complications of ocular inflammation, such as for example in the ocular infections due to *Pseudomonas aeruginosa*.

The composition of the invention, as well as the product of the invention, proved also to be useful in the treatment of dry eye syndrome and hyposphagma, in particular when the liposome comprises chitosan.

As a matter of fact, it is known that the dry eye syndrome depends on the reduction of the lactoferrin concentration in the lacrimal fluid which occurs with the aging of the eye. Advantageously, the delivery of lactoferrin in the eye through the liposome and the composition of the invention allow to restore the optimal lactoferrin concentration, thus solving this way the dry eye syndrome.

Moreover, the composition and the product of the invention, as demonstrated in the experimental section, proved to be suitable for the ocular topical administration, since they do not cause irritation following their administration and are highly tolerated in the ocular microenvironment. Therefore, the composition of the invention, as well as the product of the invention, can be used in the prevention and/or the treatment of ocular diseases.

In the present invention, with "diseases of the eye" or "ocular diseases" it is meant those diseases which affect any structure of the eye, e.g. the structures described above, and comprise the ocular inflammatory diseases as described above.

Preferably, such diseases of the eye are dry eye syndrome, hyposphagma, conjunctivitis, chalazion, stye, blepharoconjunctivitis and keratitis.

The invention will be better understood thanks to the not limitative exemplary figures and examples, reported below.

EXPERIMENTAL SECTION

Example 1

Figure 1:
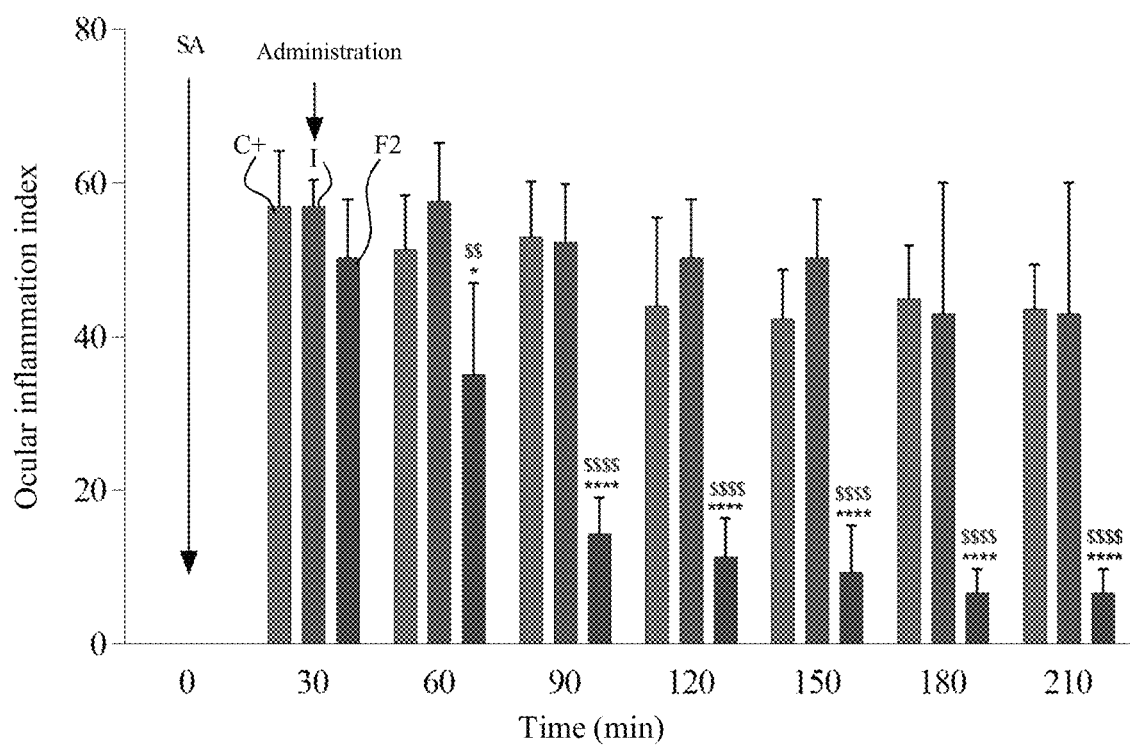
FIG. 1 shows a plot referring to the results of a test on the therapeutic activity of the products of the invention, described in detail in Example 8.

Preparation of the Products of the Invention

The liposome preparation has been carried out by means of the lipid film hydration method illustrated below. First of all, an oil phase has been prepared by adding, under stirring, the lipids forming the lipid bilayer of the liposome and other compounds (see Table 1 below for the qualitative and quantitative composition of the oil phase) to ethanol, until the formation of a homogeneous phase. Later, ethanol has been removed under reduced pressure by means of a rotary evaporator (Buchi R-210). A lipid film has been then obtained. In order to assure the complete evaporation of the solvent, the lipid film has been fully dried by using a nitrogen flux. Later, an aqueous phase has been prepared by adding to water the components which will be part of the core of aqueous solution inside the liposome (see Table 1 below for the qualitative and quantitative composition of the aqueous phase). The so prepared aqueous phase has been added to the lipid film (step of lipid film hydration) and the mixture has been homogenized by using an ultrasonic bath (Transsonic Digitals), thus obtaining the formation of liposomes. Finally, the so obtained liposomes underwent two cycles of homogenization process at 800 mbar and ambient temperature by means of the Stransted-pressure cell homogeniser-FPG12800 instrument.

According to the above described method, three formulations (F1, F2 and F3) of the products of the invention have been prepared. In F1 formulation, the liposomes comprise lactoferrin and chitosan, while in F2 and F3 compositions, the liposomes comprise lactoferrin and hyaluronic acid. For F1, chitosan has been added after the step of lipid film hydration and before the two cycles of homogenization. The qualitative and quantitative composition of F1, F2 and F3 is set forth in Table 1.

TABLE 1

| Formulation | | Component and % amount (w/v) | Oil or aqueous phase |
|---|---|---|---|
| F1 | Liposomes comprising lactoferrin and chitosan | Lipoid S75 3% | Oil phase |
| | | Cholesterol 0.1% | Oil phase |
| | | Tocopherol 0.002% | Oil phase |
| | | Chitosan 0.2% | Added later |
| | | Lactoferrin 2% | Aqueous phase |
| | | Tween ® 80 0.3% | Aqueous phase |
| F2 | Liposomes comprising lactoferrin and hyaluronic acid | Lipoid S75 3% | Oil phase |
| | | Cholesterol 0.1% | Oil phase |
| | | Tocopherol 0.002% | Oil phase |
| | | Lactoferrin 2% | Aqueous phase |
| | | Hyaluronic acid 290 kDa 0.01% | Aqueous phase |
| | | Tween ® 80 0.3% | Aqueous phase |

TABLE 1-continued

| Formulation | | Component and % amount (w/v) | Oil or aqueous phase |
|---|---|---|---|
| F3 | Liposomes comprising lactoferrin and hyaluronic acid | Lipoid S80 1.5% | Oil phase |
| | | Cholesterol 0.1% | Oil phase |
| | | Tocopherol 0.002% | Oil phase |
| | | Lactoferrin 0.8% | Aqueous phase |
| | | Hyaluronic acid 1600 kDa 0.1% | Added later |
| | | Tween ® 80 0.3% | Aqueous phase |

Example 2

Characterization of the Liposomes

Liposomes of F1 and F2 prepared according to the above Example have been characterized by determining their average size and the polydispersity index (PI) by means of DLS (using the Zeta Sizer Malvern ZS instrument), and the Z-potential (ZP) by laser Doppler electrophoresis (using the Zeta Sizer Malvern ZS instrument).

The results of the above characterizations are shown in Table 2.

TABLE 2

| Formulation | Size (nm) | PI | ZP (mV) |
|---|---|---|---|
| F1 | 79.16 ± 0.43 | 0.25 ± 0.001 | 32.9 ± 0.8 |
| F2 | 85.55 ± 0.62 | 0.20 ± 0.001 | 23.5 ± 0.4 |

The size of the F1 and F2 liposomes previously determined by DLS has been checked by transmission electron microscope analysis (TEM) after negative staining. The TEM analysis confirmed the size determined by DLS of F1 and F2 liposomes. Moreover, the TEM analysis highlighted the smooth and spherical surface of F1 and F2 liposomes.

Example 3

Preparation of Additional Liposomes

Additional liposomes have been prepared, shown in Table 3, according to the method described in Example 1. The aqueous phase and the oil phase of F1.1, F1.2, F1.3 and F1.4 liposomes qualitatively and quantitatively correspond to those of F1 formulation described in Table 1, while the aqueous phase and the oil phase of F2.1, F2.2, F2.3 and F2.4 liposomes qualitatively and quantitatively correspond to those of F2 formulation described in Table 1. To such additional liposomes, after two cycles of homogenization, have been added:

5% hydroxypropyl-β-cyclodextrin and 5% trehalose to F1.1, F1.2, F1.3 and F1.4 liposomes;

9.93% hydroxypropyl-β-cyclodextrin and 7% trehalose to F2.1, F2.2, F2.3 and F2.4 liposomes.

The liposomes of the present example have been characterized as described in Example 2. The results of such characterizations are set forth in Table 3.

TABLE 3

| Formulation | Size (nm) | PI | ZP (mV) |
|---|---|---|---|
| F1.1 | 89.95 ± 0.64 | 0.257 ± 0.009 | 34.3 ± 0.51 |
| F1.2 | 88.87 ± 0.95 | 0.259 ± 0.005 | 36.9 ± 0.66 |
| F1.3 | 89.10 ± 0.02 | 0.261 ± 0.004 | 35.7 ± 0.17 |
| F1.4 | 88.46 ± 0.64 | 0.263 ± 0.003 | 34.4 ± 0.58 |
| F2.1 | 79.71 ± 0.17 | 0.204 ± 0.01 | 20.20 ± 0.37 |
| F2.2 | 78.37 ± 0.36 | 0.200 ± 0.004 | 20.63 ± 2.10 |
| F2.3 | 78.14 ± 0.19 | 0.205 ± 0.005 | 21.84 ± 0.62 |
| F2.4 | 77.36 ± 0.10 | 0.205 ± 0.007 | 21.13 ± 0.41 |

The osmolarity values of all formulations are set forth in Table 3 and are around 300 mOsm/kg. Such values have been determined by using the Advanced® Model 3320 Micro-Osmometer instrument (Advanced® Instruments, Inc., Norwood, Mass., USA).

Example 4

Sterilization of the Liposomes

The F2 liposomes have been sterilized by using γ rays at a dose of 25 kGy.

After such sterilization, the sterilized F2 liposomes have been characterized again in order to check that the above described sterilization process does not affect their structure. The results of such characterizations are set forth in Table 4.

TABLE 4

| Formulation | Sterilization | Size (nm) | PI | ZP (mV) | Osmolarity (mOsm/kg) |
|---|---|---|---|---|---|
| F2 | Before | 85.55 ± 0.62 | 0.20 ± 0.001 | 23.5 ± 0.4 | 273 |
| | After | 92.54 ± 0.61 | 0.203 ± 0.008 | 28.5 ± 0.56 | 279 |

The results shown in Table 4 confirm that F2 liposomes do not undergo any substantial change of their characteristics after the sterilization treatment.

A sterilization treatment as described above has been carried out equally to F1 liposomes.

Example 5

Freeze-Drying Process of the Liposomes

Liposomes F1 to F1.4 and F2 to F2.4 have been freeze-dried by means of the following freeze-drying process:

TABLE 5

| Step | Time (hours) | Temperature (° C.) | Pressure (mBar) |
|---|---|---|---|
| Freezing | 8 | −80 | Atmospheric P |
| Freezing | 1 | −30 | Atmospheric P |
| Primary drying | 3 | −30 | 0.350 |
| Primary drying II | 1 | −15 | 0.350 |
| Secondary drying | 12 | +10 | 0.350 |

The freeze-drying process as described above allows the long-term storage of the liposomes, preserving the original chemical-physical characteristics after reconstitution.

Example 6

Evaluation of the In Vitro Ocular Irritation by Means of HET CAM Test

The in vitro test described in the present example has been carried out in order to evaluate if the ocular topical administration of the liposomes could cause irritation to the eye. To such purpose, the in vitro HET CAM test as described in ICCVAM-Recommended Test Method Protocol has been carried out: Hen's Egg Test-Chorioallantoic Membrane (HET-CAM) Test Method.

The HET CAM test has been carried out by observing the irritation effects (bleeding, vasoconstriction and clotting) induced on the chorioallantoic membrane (CAM) of 10 days embryonated eggs by applying 0.3 ml of liposomes under test and calculating the ocular irritation index ("OII") according to the formula described in Table 6. OII can be grouped in the four categories set forth in Table 6.

TABLE 6

| Calculation of OII (HET CAM) | OII | Classification |
|---|---|---|
| OII = (301 − H) * 5/300 + (301 − v) × 7/300 + (301 − C) * 9/300 | 0-0.9 | Not-irritant |
| | 1-4.9 | Slightly irritant |
| H: bleeding, v: vasoconstriction, C: clotting | 5-8.9 | Moderately irritant |
| | 9-21 | Irritant |

The liposomes under examination in the present test are F1 and F2 liposomes. By means of the same method, the following controls have been also tested: SDS 1% (positive control with slow irritation), 0.1 N NaOH (positive control with fast irritation) and NaCl 0.9% (negative control).

The embryonated eggs for this test have been obtained by the G.A.L.L.S.A. farm, Tarragona, Spain. The eggs are kept at a temperature of 12±1° C. for at least 24 hours before placing them into the incubator at controlled temperature (37.8° C.) and humidity (50-60%) during the incubation days.

The data have been analyzed as mean±standard deviation at the moment when the injury occurred (n=3/group).

The results of the HET CAM test demonstrated that:

SDS 1% and 0.1 N NaOH have irritating effects (both positive controls);

NaCl has not irritating effects (negative control); and

F1 and F2 liposomes have not irritating effects, have an ocular irritation index corresponding to that of the not-irritating products.

Therefore, it has been demonstrated, by means of the present in vitro test, that the products of the invention do not cause ocular irritation.

Example 7

Evaluation of the In Vitro Ocular Irritation by Means of Draize Test

The in vitro test described in the present example has been carried out in order to evaluate if the ocular topical administration of the products of the invention could cause irritation to the eye. To this purpose, the Draize irritation test has been carried out. Such test has been carried out by using male albino rabbits from New Zealand of 2.5 kg average got from the San Bernardo farm (Navarra).

The present test has been carried out by placing the sample to be evaluated inside the conjunctival sac of the left eye of the albino rabbits. A moderate massage has been carried out to guarantee the correct circulation. The occurrence of irritation has been observed both at the moment of application and after one hour, by using the right eye as negative control (n=3/group). According to the present example, the samples to be evaluated were F1 liposomes and F2 liposomes.

The evaluation of the irritation has been carried out by directly observing the anterior segment of the eye, detecting the possible injuries of conjunctiva, iris and cornea as shown in Table 8. The ocular irritation index ("OII") has been calculated based on the observed injuries and the formula set forth in Table 7.

TABLE 7

Calculation of OII (Draize test)

OII = Cornea (A * B * 5) + Iris (A * 5) + Conjunctiva (A + B + C) * 2

TABLE 8

| Structure | Injury | Evaluation | Score |
|---|---|---|---|
| CORNEA | A) Level of opacity | | Corneal score: |
| | Absence of ulcers | 0 | A * B * 5 |
| | Diffused areas | 1 | Maximum score: |
| | Translucent areas | 2 | 80 |
| | Opalescent areas | 3 | |
| | Full opacity | 4 | |
| | B) Affected area | | |
| | None | 0 | |
| | One fourth or less | 1 | |
| | More than a quarter but without means | 2 | |
| | More than half but less than three quarters | 3 | |
| | More than three quarters up to a whole plane | 4 | |
| IRIS | A) Score of the damage to iris | | Radial score: A * 5 |
| | Normal | 0 | Maximum score: |
| | Presence of deep wrinkles, congestion, puffiness, moderate circumncorneal injection | 1 | 10 |
| | No reaction to light, hemorrhage, extensive damage (injury) | 2 | |
| CONJUNCTIVA | A) Redness | | Corneal score: |
| | Normal eye | 0 | (A + B + C) * 2 |
| | Some vessels clearly injected | 1 | Maximum score: |
| | Diffused redness | 2 | 20 |
| | Highly diffused redness | 3 | |
| | B) Chemosis or inflammation | | |
| | None | 0 | |
| | Partial | 1 | |
| | Pronounced with partial dysfunction of the eyelids | 2 | |
| | Eyelids more or less closed | 3 | |
| | Eyelid dropping | 4 | |
| | C) Secretions | | |
| | None | 0 | |
| | Any anomalous amount | 1 | |
| | Humidity and wet eyelash of the eyelids | 2 | |
| | Periocular humidity | 3 | |

The results of the present test revealed that both F1 and F2 liposomes are not irritating (OII=0). Indeed, the animals did not show any in vivo sign of irritation both at the moment of application, and after one hour. The present test has therefore confirmed the results of the test of the previous Example, demonstrating that the products of the invention do not cause ocular irritation and are therefore suitable to be administered by ocular topical route.

Example 8

In Vivo Treatment of Ocular Inflammation

The ability of in vivo treatment of the inflammation by F2 liposomes by means of the below set forth irritation test has been evaluated.

Inflammation in the eye of male albino rabbits as described in Example 7 is induced by applying a drop of eye drops containing 0.5% arachidonic acid sodium salt (SA-irritating agent) at time 0. After 30 minutes, the sample under examination is administered to the inflamed eye. Finally, the ocular inflammation index is evaluated at different time points. In the present test, the samples under examination were:

I) 50 μl of free lactoferrin (not encapsulated into the lipid bilayer of liposomes) dissolved in PBS (comparative example);
II) 50 μl of F2 liposomes.

As positive control (C+-comparative), a rabbit administered with SA at time 0, without any administration after 30 minutes, has been used.

The ocular inflammation has been evaluated for each time point at 30, 60, 90, 120, 150, 180 and 210 minutes and the inflammation index has been consequently calculated for each time point according to the tables of the previous Example.

The results of the present test are shown in FIG. 1. In particular, FIG. 1 shows the values of ocular inflammation score of the positive control (C), free lactoferrin (I) and F2 liposomes at the minutes set forth above. In FIG. 1, the order of the bars represent the ocular inflammation indexes is C+, I and F2 for all the measurements at the minutes set forth above. Moreover, in FIG. 1 the comparison of F2 liposomes or free lactoferrin (I) to the positive control (C+) is represented as *$p<0.05$,  $p<0.01$, * $p<0.001$, **** $p<0.0001$, while the comparison of F2 liposomes to the free lactoferrin (I) is represented as $^\$p<0.05$, $^{\$\$}p<0.01$, $^{\$\$\$}p<0.001$, $^{\$\$\$\$}p<0.0001$. The results shown in FIG. 1 demonstrate that the product of the invention, in particular that one comprising the hyaluronic acid (F2), is effective in treating the ocular inflammation. In particular, the products of the invention proved to be particularly effective in the treatment of inflammation already after 60 minutes from their administration. The products of the invention proved also to be surprisingly more effective than free lactoferrin in the treatment of inflammation also in the long-term, possibly as a consequence of the sustained release of lactoferrin and hyaluronic acid.

Example 9

In Vivo Prevention of Ocular Inflammation

The ability of in vivo prevention of the inflammation by F1 and F2 liposomes by means of the below set forth irritation test has been evaluated.

The samples under examination are applied at time 0 to the eye of male albino rabbits as described in Example 7. After 30 minutes, a drop of eye drops containing 0.5% arachidonic acid sodium salt (SA-irritating agent) is applied to the same eye. Finally, the ocular inflammation index is evaluated at different time points. In the present test, the samples under examination were F1 liposomes and F2 liposomes. As positive control (C+-comparative), a drop of eye drops containing 0.5% arachidonic acid sodium salt (SA-irritating agent) has been applied to the eye of a male albino rabbit at minute 30, without prior application of any liposome.

The ocular inflammation has been evaluated for each time point at 60, 90, 120, 150, 180 and 210 minutes after the administration of F1 and F2 formulations and the inflammation index (OII) has been consequently calculated for each point in time according to the tables of Example 7.

Figure 2:
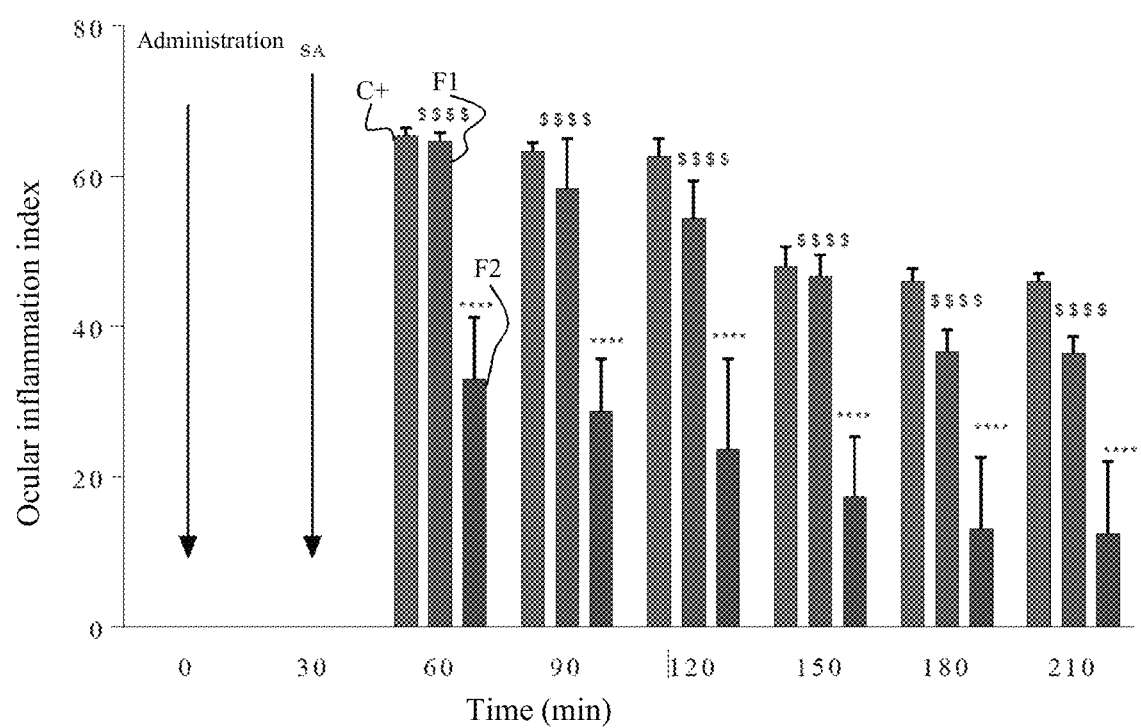
FIG. 2 shows a plot referring to the results of a test on the prophylactic activity of the products of the invention, described in detail in Example 9.

The results of the present test are shown in the plot of FIG. 2. In particular, FIG. 2 shows the values of ocular inflammation score of the positive control (C+), the formulation of F1 liposomes, and the formulation of F2 liposomes, at the minutes set forth above. In FIG. 2, the order of the bars representing the ocular inflammation indexes is C+, F1 and F2 for all the measurements at the minutes set forth above.

Moreover, in FIG. 2, the values are expressed as mean±standard deviation, *$p<0.05$, $p<0.01$, *$p<0.001$ and ****$p<0.0001$ significantly lower than the inflammatory effects induced by SA; the values are expressed as mean±standard deviation, $^\$p<0.05$, $^{\$\$}p<0.01$, $^{\$\$\$}p<0.001$ and $^{\$\$\$\$}p<0.0001$ significantly lower than the inflammatory effect induced by the other liposome formulations developed.

The results shown in FIG. 2 demonstrate that there is efficacy in the prevention of ocular inflammation of liposomes of F1 and F2 formulations; in particular, for the formulations of liposomes comprising hyaluronic acid (F2). Such efficacy in the prevention of the inflammation is present already 30 minutes after the inflammatory stimulus of the liposomes comprising hyaluronic acid. In addition the results show that F1 liposomes comprising chitosan provide better results with respect to C+ positive control and require longer time to provide the prevention effect with respect to F2 liposomes comprising hyaluronic acid. It is believed that this is due to the gradual and sustained release of lactoferrin characterizing the products of the invention comprising chitosan.

Example 10

Hyposphagma Treatment

The present test has been carried out in order to determine the reduction level of hyposphagma by the products of the invention. According to the present test, hyposphagma has been induced in the rabbit by means of the method described below. The reduction level of hyposphagma has been evaluated by using biodegradable systems and controlled administration.

The test has been performed on 9 rabbits. In order to realize this test, the rabbis have been administered with an intramuscular anesthesia (ketamine/xylazine) and an ocular topical anesthesia (procaine in drops). Once the rabbits have been anesthetized, the fur of one of the two ears has been shaved and then the shaved ear has been cleaned with alcohol. From the auricular marginal vein 0.2 ml of blood has been extracted, and immediately after the extraction, 0.1 ml of the previously extracted blood has been injected in the superior conjunctival area of the rabbit eye. The rabbits have then been randomly sorted in 3 different groups, to which different treatments in the form of ocular drops have been applied:

I) control group: Saline serum (positive control);
II) ocular drops of liposomes comprising lactoferrin and hyaluronic acid (F2 liposomes); and
III) ocular drops of liposomes comprising lactoferrin and chitosan (F1 liposomes).

Once the rabbit has been reawakened, the reduction level of hyposphagma with respect to the control group (as described below) after 8, 24, 48, 72, 96 and 120 hours following the induction of the same has been evaluated. The treatment with ocular drops is applied daily. Hyposphagma is evaluated with a millimetric scale at time zero and during its daily evolution by the treatment. Later the rabbit will be sacrificed by means of anesthesia followed by a pentobarbital dose. The obtained results have been analyzed by using an ANOVA test to observe if significant effects are produced with respect to the control group.

The preliminary results deriving from what reported in the present example have demonstrated a greater efficacy of F2 and F1 with respect to the control group in the treatment of hyposphagma.

Example 11

Treatment of Dry Eye

The present test has been carried out in order to determine the reduction level of dry eye by the products of the invention. According to the present test, dry eye has been induced in the rabbit by means of the method described below. The reduction level of dry eye has been evaluated by using biodegradable systems and controlled administration.

The test has been performed on 9 rabbits. During the first 3 weeks, the rabbit has been treated with ocular drops of 0.1% benzalkonium chloride two times per day (morning and afternoon, weekend included). This treatment is required to guarantee a statistically significant effect (n=3/group). After the three weeks of preparation, the treatment has been applied (see the following bulleted list) during one week. The rabbits have been randomly sorted in 3 different groups:

I) control group: Saline serum (positive control);
II) ocular drops of liposomes comprising lactoferrin and hyaluronic acid (F2 liposomes); and
III) ocular drops of liposomes comprising lactoferrin and chitosan (F1 liposomes).

At the end of the treatment, the Schirmer test and the staining with fluorescein (under anesthesia) have been performed in order to evaluate the extension of the treatment of dry eye for each single group. Later the rabbits have been sacrificed.

The preliminary results of the present example have demonstrated a greater efficacy of F2 and F1 with respect to the control group in the treatment of dry eye.

The invention claimed is:

1. A product made of liposomes, which comprises lactoferrin and a component selected from hyaluronic acid or chitosan, for its use in the prevention and/or treatment of ocular diseases.

2. The product according to claim 1, characterized in that said ocular diseases are inflammatory ocular diseases selected from the group comprising conjunctivitis, chalazion, stye, blepharoconjunctivitis and keratitis.

3. The product according to claim 1, characterized in that said ocular diseases are selected from the group comprising dry eye syndrome and hyposphagma.

4. The product according to claim 1, characterized in that said liposomes have a positive Z-potential charge, preferably said Z-potential charge is greater than or equal to 10 mV, more preferably it is greater than or equal to 15 mV, still more preferably it is greater than or equal to 20 mV.

5. The product according to claim 1, characterized in that said liposomes have a size lower than or equal to 200 nm.

6. The product according to claim 1, characterized in that the core of aqueous solution inside said liposomes has an osmolarity in the range from 200 to 500 mOsm/Kg.

7. A product made of liposomes, which comprises lactoferrin and a component selected from hyaluronic acid or chitosan, characterized in that said liposomes have a size lower than or equal to 200 nm, and that the core of aqueous solution inside said liposomes has an osmolarity in a range from 200 to 500 mOsm/Kg.

8. A composition comprising the product as described in claim 7 and pharmaceutically suitable excipients.

9. The composition according to claim 8, characterized in that it is an ocular topical composition.

10. The composition according to claim 8, characterized in that it comprises:
I) liposome-forming lipids in an amount in the range from 1% to 5%; and
II) lactoferrin in an amount in the range from 0.5% to 8%; and a component selected from
III) hyaluronic acid in an amount in the range from 0.0001% to 0.5%; or
IV) chitosan in an amount in the range from 0.02% to 2%.

* * * * *